(12) United States Patent
Binier (10) Patent No.: US 10,052,439 B2
(45) Date of Patent: Aug. 21, 2018

(54) RESETTING MECHANISM FOR DRUG DELIVERY DEVICE AND RESETTABLE DRUG DELIVERY DEVICE

(71) Applicant: INNOVATIVE PRECISION INSTRUMENTS LIMITED, Hong Kong (HK)

(72) Inventor: Richard Jean Marie Binier, Taipei (TW)

(73) Assignee: INNOVATIVE PRECISION INSTRUMENTS LIMITED, Hong Kong (HK)

( * ) Notice: Subject to any disclaimer, the term of this patent is extended or adjusted under 35 U.S.C. 154(b) by 0 days.

(21) Appl. No.: 15/873,656

(22) Filed: Jan. 17, 2018

(65) Prior Publication Data
US 2018/0161509 A1 Jun. 14, 2018

Related U.S. Application Data

(63) Continuation of application No. PCT/CN2016/104025, filed on Oct. 31, 2016.

(51) Int. Cl.
*A61M 5/00* (2006.01)
*A61M 5/315* (2006.01)
*A61M 5/24* (2006.01)

(52) U.S. Cl.
CPC .... *A61M 5/31543* (2013.01); *A61M 5/31545* (2013.01); *A61M 5/31576* (2013.01); *A61M 2005/2488* (2013.01)

(58) Field of Classification Search
CPC ....... A61M 5/31543; A61M 5/20; A61M 5/24
See application file for complete search history.

(56) References Cited

U.S. PATENT DOCUMENTS 6,277,099 B1 * 8/2001 Strowe .............. A61M 5/31553
604/186

* cited by examiner

*Primary Examiner* — Laura Bouchelle
(74) *Attorney, Agent, or Firm* — Kramer & Amado, P.C.

(57) ABSTRACT

Various embodiments relate to a resetting mechanism for resetting a screw spindle of a drug delivery device including a driving element including two opposite driving pillars, connected to a sidewall and disposed in a chamber, a limiting element, movably engaged with the driving element, and two opposite clamping elements, movably disposed on two sides of the screw spindle, each of the clamping elements including a sliding base wherein the sliding base has a guide rail and a recess and a clamping jaw, connected to the sliding base and disposed in the chamber, wherein the opposite driving pillars slide in the guide rails along with the movement of the driving element, when the driving element moves toward the limiting element, the driving pillars drive the two clamping elements to move toward the screw spindle to make the two clamping jaws clamp the screw spindle and when the driving element moves away from the limiting element, the driving pillars drive the two clamping elements to move away from the screw spindle to make the two clamping jaws release the screw spindle.

24 Claims, 8 Drawing Sheets

RESETTING MECHANISM FOR DRUG DELIVERY DEVICE AND RESETTABLE DRUG DELIVERY DEVICE

TECHNICAL FIELD

The present disclosure is directed to a resetting mechanism for a drug delivery device and a resettable drug delivery device having the resetting mechanism.

BACKGROUND

Patients with chronic diseases are often prescribed drugs which may be taken hourly, daily, weekly, etc. and therefore, a pen type drug delivery device was developed to provide the patient, who does not have formal medical training, to perform self-injection periodically.

Currently, there are two types of pen type drug delivery devices, namely, disposable (i.e., non-resettable) and reusable (i.e., resettable). These types of pen delivery devices are generally comprised of three primary elements: (i) a cartridge section that includes a cartridge contained within a holder; (ii) a needle assembly connected to one end of the cartridge section; and (iii) a dosing section connected to the other end of the cartridge section.

The cartridge includes a reservoir that is filled with a drug (e.g., insulin), a movable rubber type bung located at one end of the cartridge reservoir, and a top having a pierceable rubber seal located at the other end. While the cartridge housing may be typically made of plastic, cartridge reservoirs have historically been made of glass.

The dosing section is the portion of the pen device that is used to set a dose. During an injection, a screw spindle contained within the dosing section presses against the bung of the cartridge. This force causes the drug contained within the cartridge to be injected through an attached needle assembly.

Disposable pen delivery devices do not have removable pre-filled cartridges. Rather, the pre-filled cartridges may not be removed and replaced from these devices without destroying the device itself. Therefore, these disposable devices do not need to have a resettable dose setting mechanism.

In contrast to disposable pen delivery devices, typical reusable pen delivery devices feature two main reusable components, namely, a cartridge holder and a dose setting mechanism.

After a cartridge is inserted into the cartridge holder, the cartridge holder is attached to the dose setting mechanism. The user may use the dose setting mechanism to select a dose. After the drug in the cartridge has been exhausted, the user may detach the cartridge housing from the dose setting mechanism. The user may then remove the empty cartridge from the cartridge holder and replace the empty cartridge with a new cartridge.

In order to reset the reusable pen delivery device, aside from replacing the empty cartridge with a new cartridge, the dose setting mechanism must be reset to an initial position. For example, in certain typical reusable pen delivery devices, in order to reset the dose setting mechanism, the screw spindle that advances in a distal direction during dose injection must be retracted back into the dose setting mechanism.

Known reset mechanisms require a user to push back (i.e., retract) the screw spindle or some other portion of the dose setting mechanism back into the mechanism.

Known reusable pen delivery devices have certain perceived disadvantages. One perceived disadvantage is that the user has to disassemble the device to either remove an empty cartridge or reset the device. Another perceived disadvantage is that such devices have an increased number of parts and therefore such devices are typically complicated from a manufacturing and from an assembly standpoint.

For example, known reusable pen type devices are not intuitive as to how a user may replace an empty cartridge and reset the device. In addition, because such reusable devices use a large number of components, such reusable devices tend to be large and bulky, and therefore not easy to carry around or transport.

SUMMARY OF EXEMPLARY EMBODIMENTS

A brief summary of various embodiments is presented below. Embodiments address the need to create a resettable mechanism and a resettable drug delivery device.

In order to overcome these and other shortcomings of the prior art and in light of the need to create a resetting mechanism and a resettable drug delivery device, which can simplify the steps for a user to reset the screw spindle and reduce production costs, a brief summary of various exemplary embodiments is presented.

Detailed descriptions of a preferred exemplary embodiment adequate to allow those of ordinary skill in the art to make and use the inventive concepts will follow in later sections.

Various embodiments described herein relate to a resetting mechanism for resetting a screw spindle of a drug delivery device including a driving element including two opposite driving pillars connected to a sidewall and disposed in a chamber, a limiting element movably engaged with the driving element and two opposite clamping elements movably disposed on two sides of the screw spindle, each of the clamping elements including a sliding base, wherein the sliding base has a guide rail and a recess, and a clamping jaw, connected to the sliding base and disposed in the chamber, wherein the opposite driving pillars slide in the guide rails along with the movement of the driving element, when the driving element moves toward the limiting element, the driving pillars drive the two clamping elements to move toward the screw spindle to make the two clamping jaws clamp the screw spindle, when the driving element moves away from the limiting element, the driving pillars drive the two clamping elements to move away from the screw spindle to make the two clamping jaws release the screw spindle.

In an embodiment of the present disclosure, the resetting mechanism includes the driving element, further including a base having an opening for the screw spindle to insert through, a sidewall surrounding the base to form a chamber, wherein the sidewall has two opposite first notches and two opposite second notches and two opposite positioning pillars connected to the sidewall and disposed on the two opposite first notches.

In an embodiment of the present disclosure, the resetting mechanism includes the limiting element, further including an annular case, configured to cooperate the chamber wherein the annular case allows the screw spindle to insert therethrough, two opposite limiting arms, connected to the annular case and configured to cooperate with the two opposite first notches, wherein each of the two opposite limiting arms includes a passage along a length direction of the each of the two opposite limiting arms and two opposite positioning blocks, connected to the annular case, the two positioning blocks corresponding to the two opposite second notches.

In an embodiment of the present disclosure, the resetting mechanism further includes two spring elements, sleeved on the two opposite positioning pillars and received in the passages.

In an embodiment of the present disclosure, each of the two opposite limiting arms includes a hook portion.

In an embodiment of the present disclosure, each of the guide rails extends away from a side of the sliding base near the screw spindle to a side of the sliding base away the screw spindle.

In an embodiment of the present disclosure, each of the clamping jaws has a clamping surface wherein the clamping surface includes at least one groove cooperating with a thread of the screw spindle.

In an embodiment of the present disclosure, the moving direction of the driving element is perpendicular to moving direction of the two opposite clamping elements.

In an embodiment of the present disclosure, when each of the two spring elements abuts against the driving element, each of the two spring elements apply to the driving element a thrust to move along a direction away from the limiting element.

In an embodiment of the present disclosure, the drug delivery device comprises a cylindrical case, wherein the outer wall of the cylindrical case has at least one slot for being jointed with a hook portion.

Various embodiments described herein relate to a drug delivery device, including an outer case, a drug expelling mechanism, disposed in the outer case and configured to set and dispense a dose amount of drug to be expelled, wherein the drug expelling mechanism at least comprises a cylindrical case, a resetting mechanism according to claim 1, disposed in the outer case and connected to one end of the cylindrical case and a screw spindle, inserted in the drug expelling mechanism and the resetting mechanism.

In an embodiment of the present disclosure, the drug delivery device includes the driving element, further including a base, having an opening for the screw spindle to insert through, a sidewall, surrounding the base to form a chamber wherein the sidewall has two opposite first notches and two opposite second notches and two opposite positioning pillars, connected to the sidewall and disposed on the two opposite first notches.

In an embodiment of the present disclosure, the drug delivery device including the limiting element, further including an annular case, configured to cooperate the chamber wherein the screw spindle is inserted through the annular case, two opposite limiting arms, connected to the annular case and configured to cooperate with the two opposite first notches, wherein each of the two opposite limiting arms includes a passage along a length direction of the each of the two opposite limiting arms and two opposite positioning blocks, connected to the annular case, the two positioning blocks corresponding to the two opposite second notches.

In an embodiment of the present disclosure, the drug delivery device including two spring elements, sleeved on the two opposite positioning pillars and received in the passages.

In an embodiment of the present disclosure, each of the two opposite limiting arms includes a hook portion.

In an embodiment of the present disclosure, each of the guide rails extends away from a side of the sliding base near the screw spindle to a side of the sliding base away the screw spindle.

In an embodiment of the present disclosure, each of the clamping jaws has a clamping surface wherein the clamping surface includes at least one groove cooperating with a thread of the screw spindle.

In an embodiment of the present disclosure, the moving direction of the driving element is perpendicular to the moving direction of the two opposite clamping elements.

In an embodiment of the present disclosure, when each of the two spring elements abuts against the driving element, each of the two spring elements apply to the driving element a thrust to move along a direction away from the limiting element.

In an embodiment of the present disclosure, the drug delivery device comprises a cylindrical case, wherein the outer wall of the cylindrical case has at least one slot for being jointed with a hook portion.

In an embodiment of the present disclosure, the drug delivery device further including a cartridge holder, removably connected to the outer case, wherein the cartridge holder serves to hold a cartridge, and the screw spindle is operably engaged with a piston of the cartridge.

In an embodiment of the present disclosure, when the cartridge holder is connected to the outer case, the cartridge abuts against the base of the driving element to make two clamping jaws clamp the screw spindle.

In an embodiment of the present disclosure, when the cartridge holder is not connected to the outer case, the two clamping jaws release the screw spindle to allow the screw spindle retract back to an initial position in the drug expelling mechanism.

In an embodiment of the present disclosure, the drug delivery device is an electronic insulin pen including a motor drive module.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

These and other more detailed and specific features are more fully disclosed in the following specification, reference being had to the accompanying drawings, in which.

DETAILED DESCRIPTION OF THE INVENTION

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. Descriptors such as "first," "second," "third," etc., are not meant to limit the order of elements discussed, are used to distinguish one element from the next, and are generally interchangeable.

There is a need to create a resettable drug delivery device mechanism which overcomes the disadvantages associated with resetting issues of known drug delivery devices. The resettable drug delivery devices in the present invention would reduce the number of component parts and reduce manufacturing costs while making the device less complex to assemble and manufacture. The resettable drug delivery device would also simplify the steps required for a user to reset a dose setting mechanism.

Figure 1A:
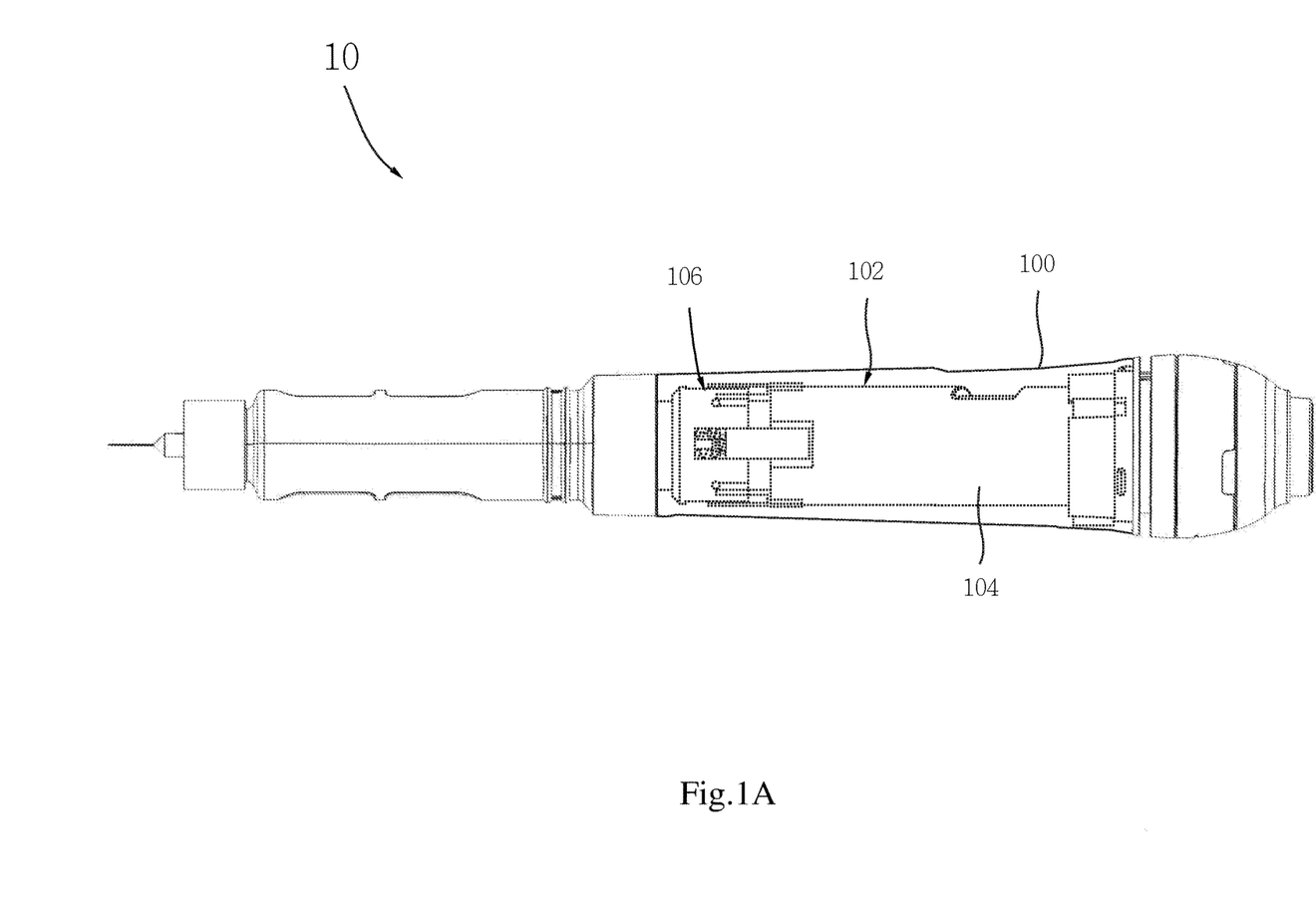
FIG. 1A illustrates a partial perspective view of a drug delivery device including a resetting mechanism according to an embodiment of the present invention.

FIG. 1A illustrates a partial perspective view of a drug delivery device including a resetting mechanism according to an embodiment of the present invention.

Figure 1B:
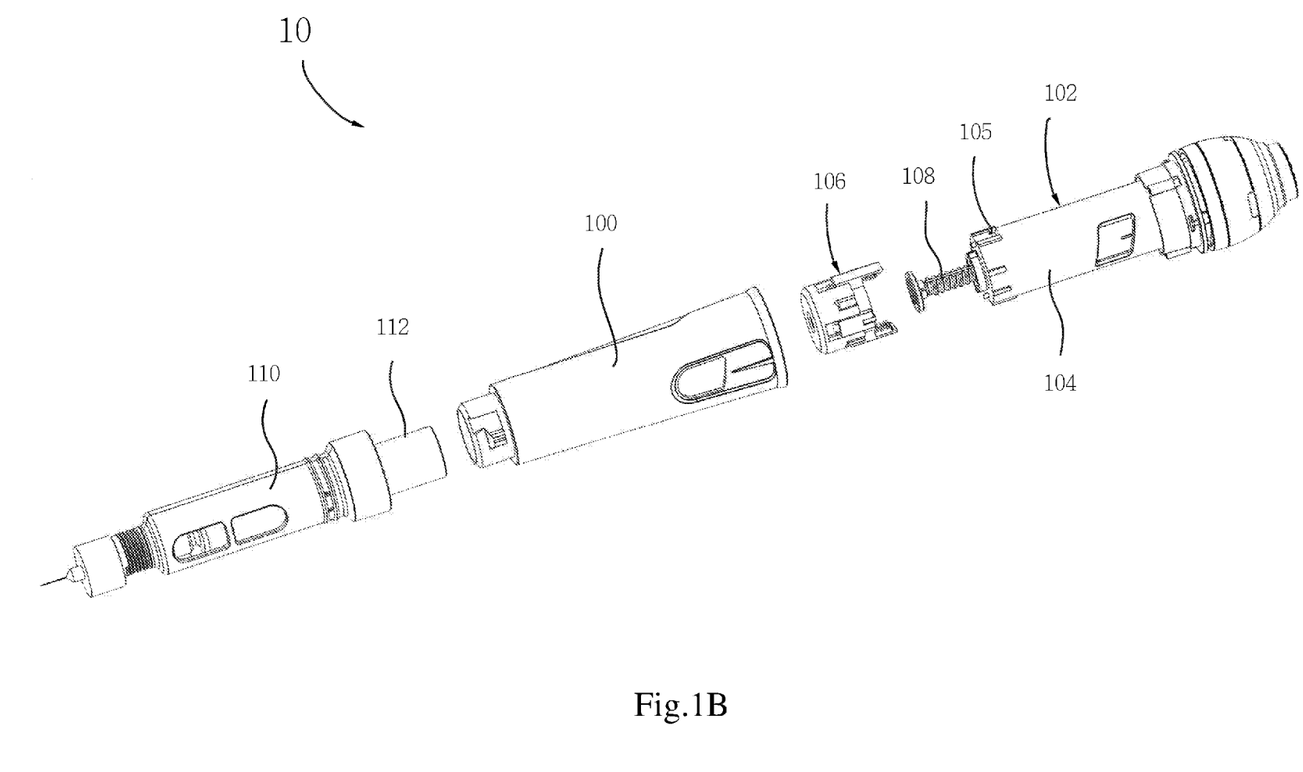
FIG. 1B illustrates an exploded view of the drug delivery device shown in FIG. 1A.
Figure 1C:
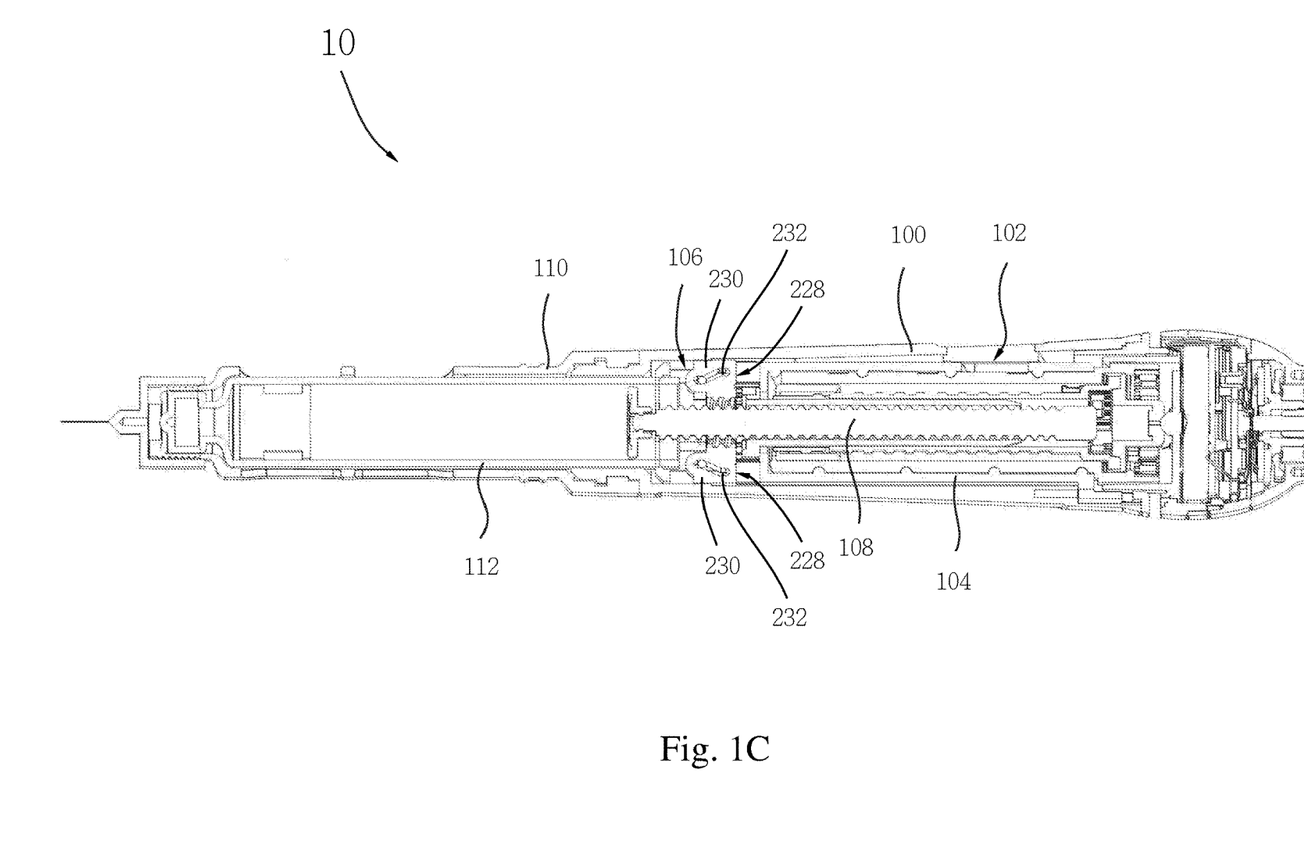
FIG. 1C illustrates a cross-sectional view of the drug delivery device shown in FIG. 1A.

FIG. 1C illustrates a cross-sectional view of the drug delivery device from FIG. 1A.

FIG. 1A illustrates the drug delivery device 10 including an outer case 100, a drug expelling mechanism 102, a resetting mechanism 106 and a screw spindle 108. The drug expelling mechanism 102 is disposed in the outer case 100, and configured to set and dispense a dose amount of drug to be expelled, wherein the drug expelling mechanism 102 includes a cylindrical case 104.

The resetting mechanism 106 is disposed in the outer case 100 and connected to one end of the cylindrical case 104. The screw spindle 108 is inserted in the drug expelling mechanism 102 and the resetting mechanism 106.

FIG. 1B illustrates an exploded view of the drug delivery device shown in FIG. 1A. As shown in FIG. 1B, an outer wall of the cylindrical case 104 has at least one slot 105. In addition, the drug delivery device 10 further includes a cartridge holder 110 that is removably connected to the outer case 100, wherein the cartridge holder 110 serves to hold a cartridge 112. Furthermore, the screw spindle 108 is operably engaged with a piston (not shown) of the cartridge 112.

Figure 2A:
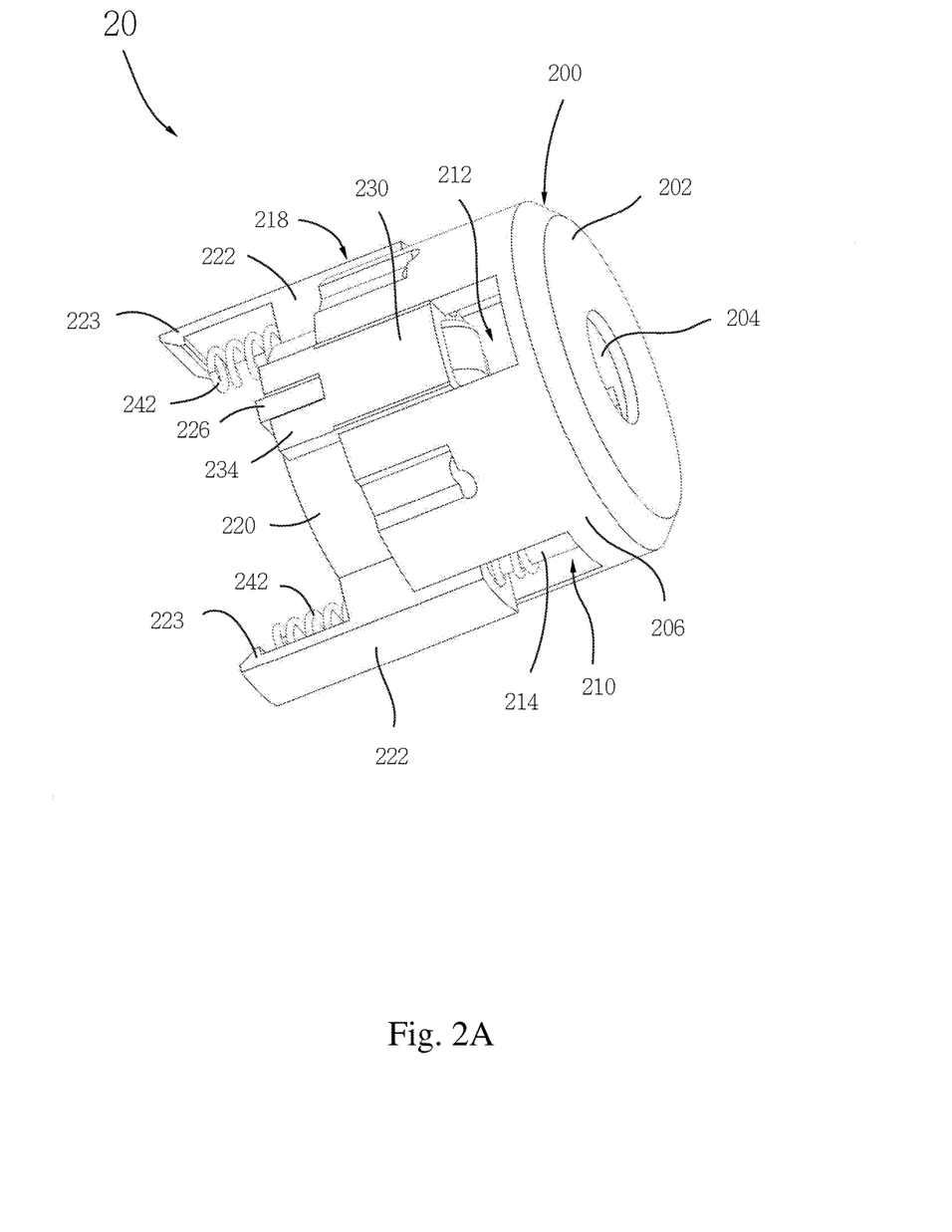
FIG. 2A illustrates a schematic view of the appearance of the resetting mechanism of the present invention.

FIG. 2A illustrates a schematic view of the appearance of the resetting mechanism of the present invention.

Figure 2B:
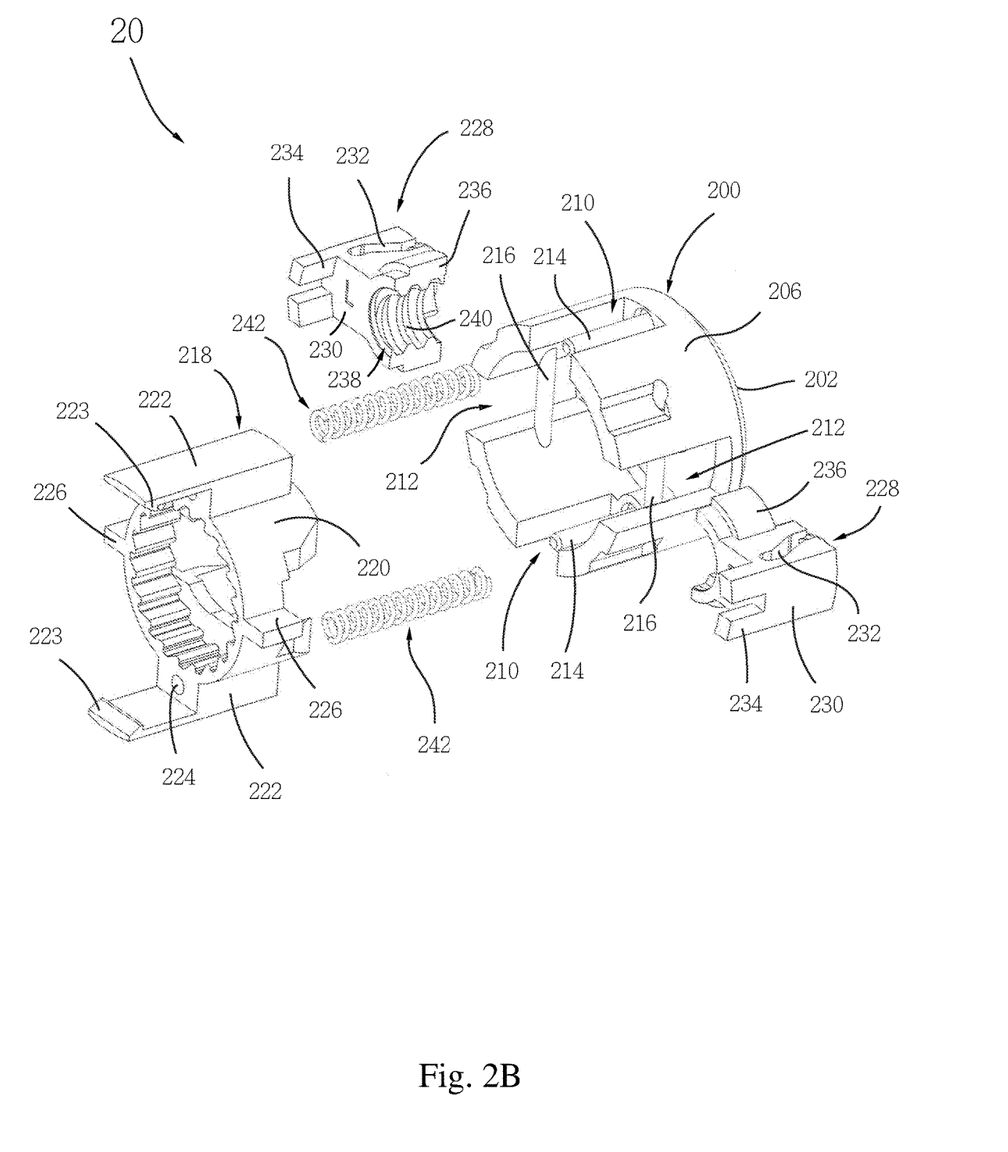
FIG. 2B illustrates an exploded view of the resetting mechanism of the present invention.

FIG. 2B illustrates an exploded view of the resetting mechanism of the present invention. The resetting mechanism 20 of the present invention may be used to reset a screw spindle of a drug delivery device, such as the screw spindle 108 of the drug delivery device 10 shown in FIG. 1B, but the present invention is not limited thereto.

The resetting mechanism 20 includes a driving element 200, a limiting element 218, two opposite clamping elements 228 and two spring elements 242.

The driving element 200 may include a base 202, a sidewall 206, two opposite positioning pillars 214 and two opposite driving pillars 216. The base 202 has an opening 204 through which the screw spindle 108 is inserted through. The sidewall 206 surrounds the base 202 to form a chamber 208, wherein the sidewall 206 has two opposite first notches 210 and two opposite second notches 212. The two opposite positioning pillars 214 are connected to the sidewall 206 and are respectively disposed on the two first notches 210. The two opposite driving pillars 216 are connected to the sidewall 206 and disposed in the chamber 208.

The limiting element 218 movably engages with the driving element 200. The limiting element 218 includes an annular case 220, two opposite limiting arms 222 and two opposite positioning blocks 226. The contour of the annular case 220 cooperates with the chamber 208 and the annular case 220 which allows the screw spindle 108 to be inserted therethrough.

The two opposite limiting arms 222 are connected to the annular case 220 and configured to cooperate with the two first notches 210. Each of the limiting arms 222 includes a passage 224 along a length direction of the each of the limiting arms 222. In addition, each of the limiting arms 222 has a hook portion 223 which can be joined with a slot 105 of the cylindrical case 104. The two opposite positioning blocks 226 are connected to the annular case 220 and corresponding to the two second notches 212.

As shown in FIG. 1C, the two opposite clamping elements 228 are movably disposed on two sides of the screw spindle 108.

Each of the clamping elements 228 includes a sliding base 230 and a clamping jaw 236. The sliding base 230 inserts in the second notch 212, and the sliding base 230 has a guide rail 232 for sliding the driving pillar 216 and a recess 234 which is configured to cooperate with the positioning block 226.

The guide rail 232 extends away from a side of the sliding base 230 near the screw spindle 108 to a side of the sliding base 230 away the screw spindle 108. The clamping jaw 236 is connected to the sliding base 230 and disposed in the chamber 208.

The clamping jaw 236 includes a clamping surface 238, and the clamping surface 238 has at least one groove 240 which is configured to cooperate with the thread of the screw spindle 108.

The two spring elements 242 are sleeved on the two positioning pillars 214 respectively and received in the passages 224. In FIG. 1B, one end of the spring element 242 can be supported on a top surface of the cylindrical case 104. Therefore, when the spring element 242 abuts against the driving element 200, the spring element 242 will apply a thrust on the driving element 200 to move along a direction away from the limiting element 218.

The annular case 220 cooperates with the chamber 208, the limiting arm 222 cooperates with the first notch 210, the recess 234 cooperates with the positioning block 226, and the sliding base 230 cooperates with the second notch 212.

Figure 3A:
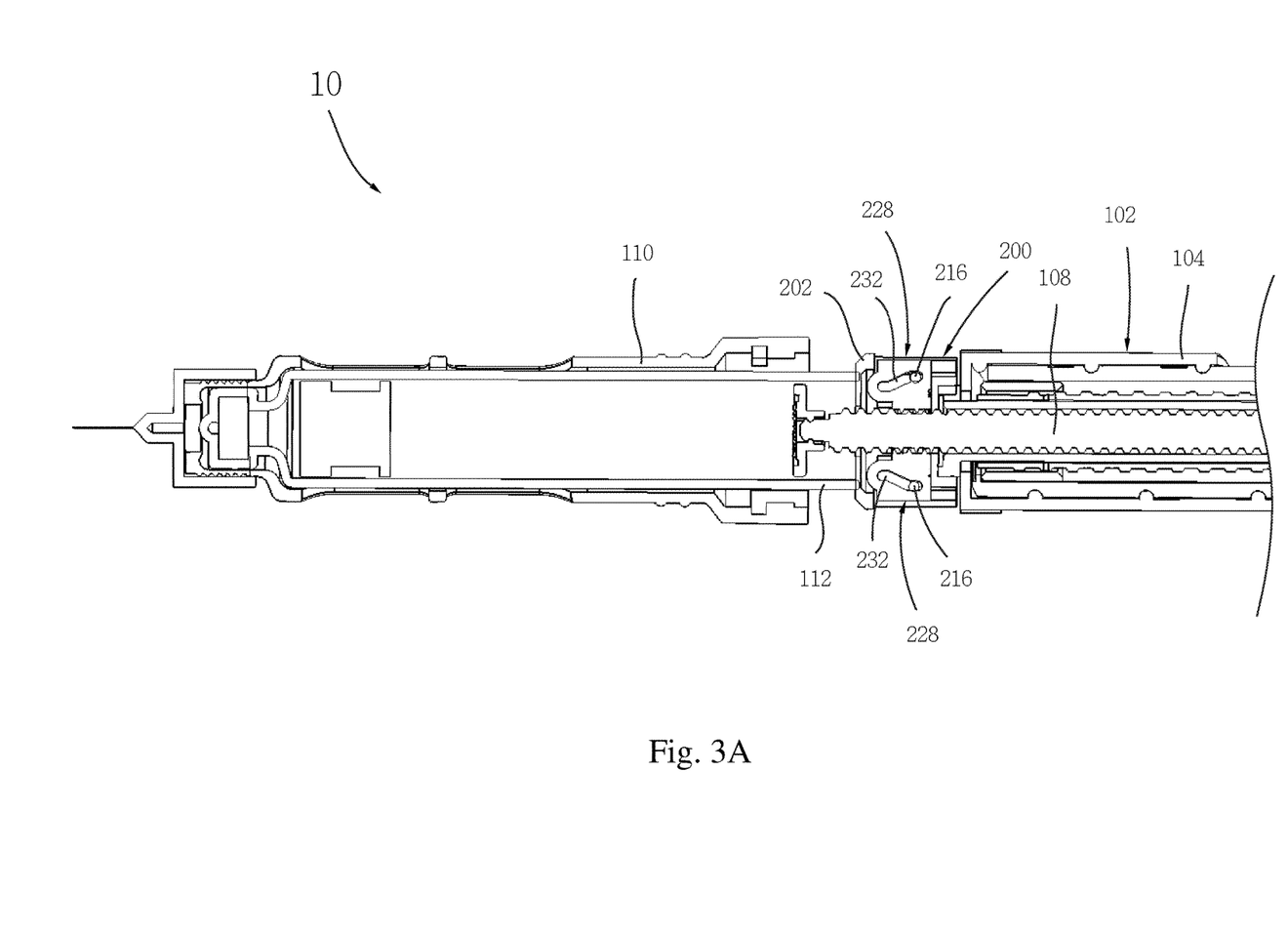
FIG. 3A illustrates a schematic view of state of use of the drug delivery device having the resetting mechanism of the present invention.
Figure 3B:
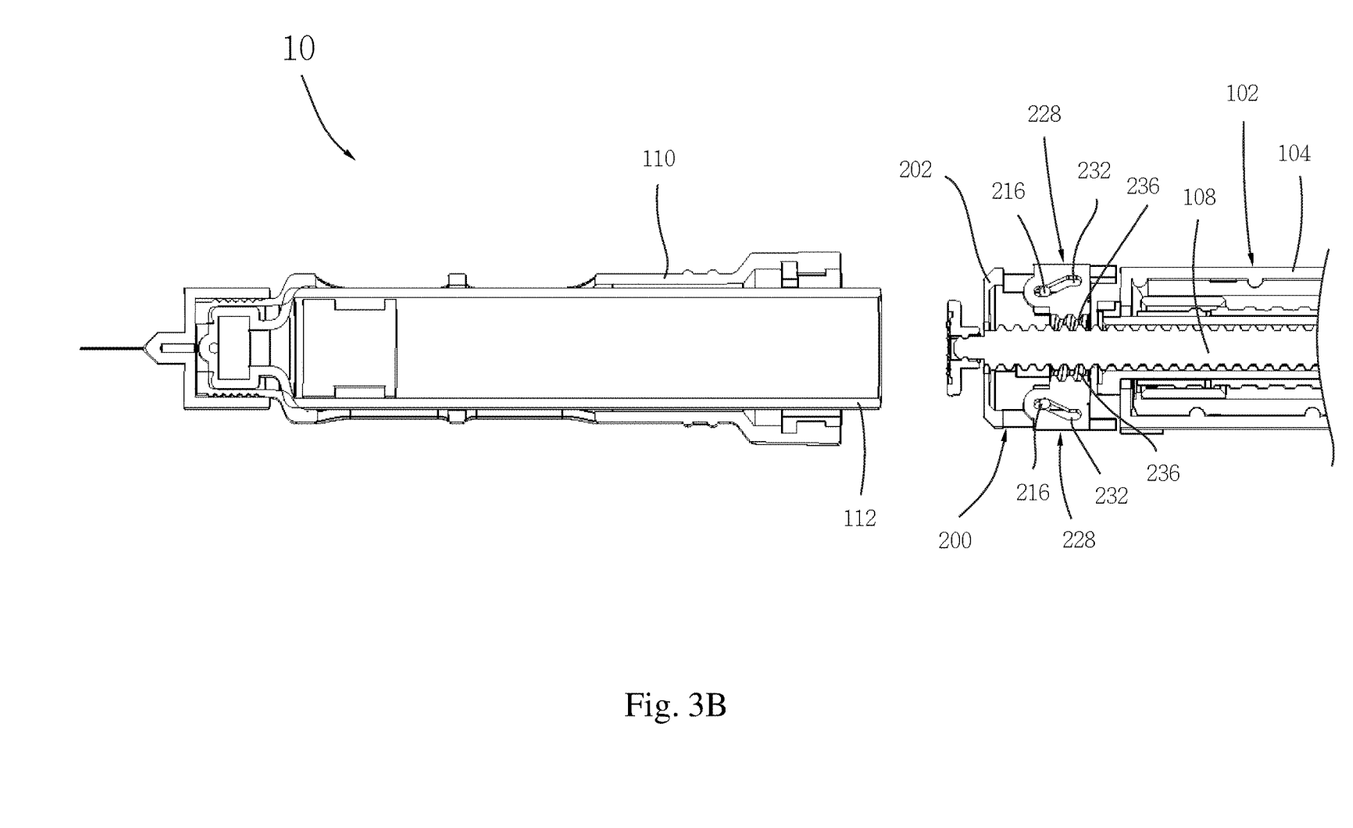
FIG. 3B illustrates a schematic view of another state of use of the drug delivery device having the resetting mechanism of the present invention.

In FIGS. 3A and 3B, the outer case 100 and the limiting element 218 are omitted.

FIG. 3A illustrates a schematic view of the use of the drug delivery device having the resetting mechanism of the present invention.

When the driving element 200 moves toward the limiting element 218, the driving pillars 216 slide in the guide rails 232 along with the movement of the driving element 200, and the driving pillars 216 drive the two clamping elements 228 to move towards the screw spindle 108 to make the two clamping jaws 236 clamp the screw spindle 108.

As shown in FIG. 3A, when the cartridge holder 110 is connected to the outer case 100, the cartridge 112 abuts against the base 202 of the driving element 200 to make the two clamping jaws 236 clamp the screw spindle 108.

FIG. 3B illustrates a schematic view of another state of use of the drug delivery device having the resetting mechanism of the present invention. When the driving element 200 moves away from the limiting element 218, the driving pillar 216 slide in the guide rails 232 along with the movement of the driving element 200, and the driving pillars 216 drive the two clamping elements 228 to move away from the screw spindle 108 to make the two clamping jaws 236 release the screw spindle 108.

As shown in FIG. 3B, when the cartridge holder 110 is not connected to the outer case 100, the two clamping jaws 236 release the screw spindle 108 to allow the screw spindle 108 retract back to an initial position in the drug expelling mechanism 102. As can be seen from FIGS. 3A and 3B, the moving direction of the driving element 200 is perpendicular to the moving direction of the clamping element 228.

Figure 4:
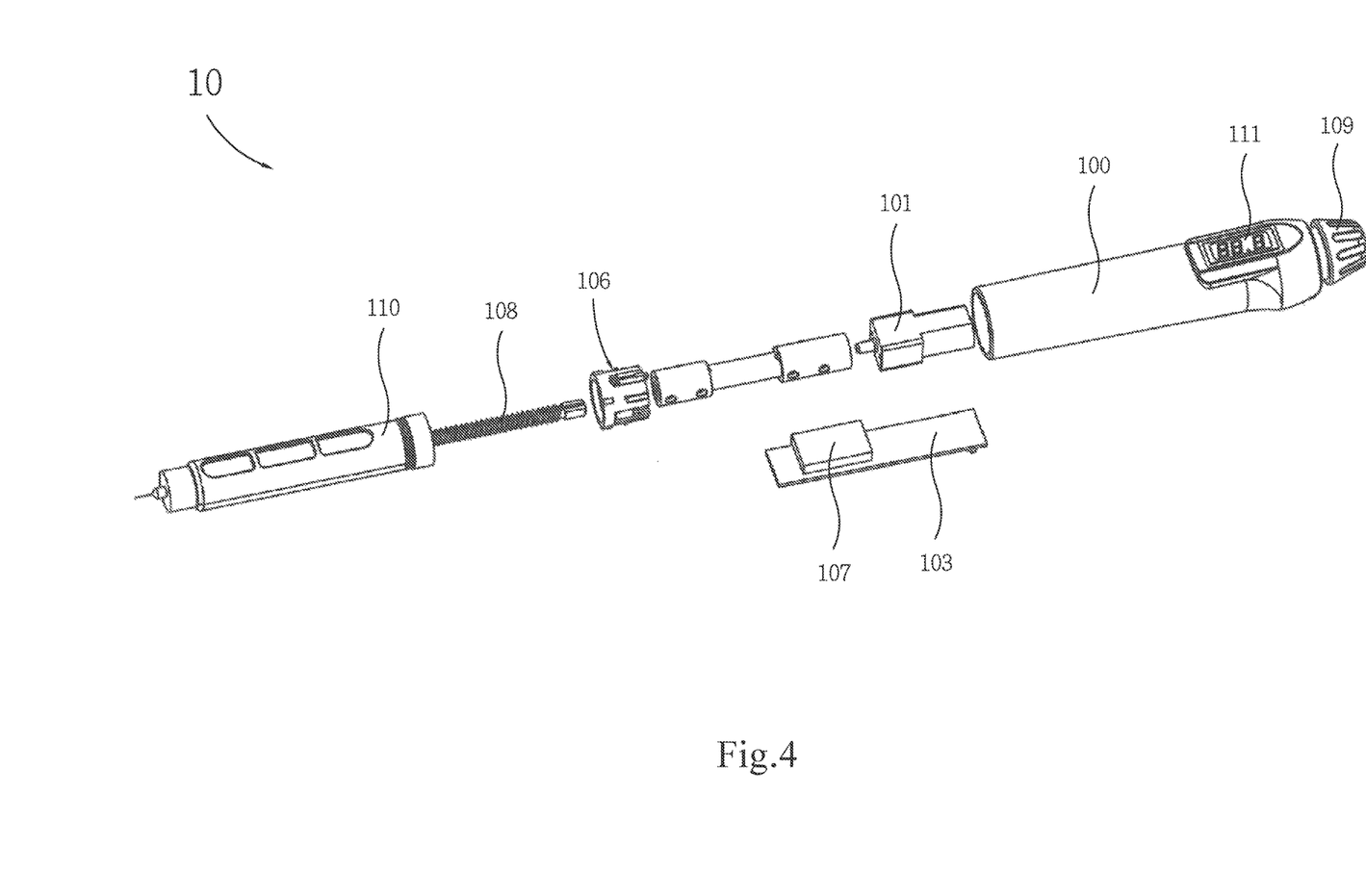
FIG. 4 illustrates an exploded view of an alternative embodiment of a syringe having the resetting mechanism of the present embodiment.

FIG. 4 illustrates an exploded view of an alternative embodiment of a syringe having the resetting mechanism of the present embodiment.

Elements corresponding to elements in the embodiment described with references to the FIGS. 1A-1C are provided with the same reference numbers.

FIG. 4 illustrates an alternative embodiment of the drug delivery device 10 with a motor drive module 101 and a control board 103. The motor drive module 101 comprises a motor and an associated drive mechanism. Furthermore, the motor drive module 101 drives the screw spindle 108 by way of a gear train (not illustrated). The control board 103 is configured for controlling the motor drive module 101 and charging a battery 107.

The resetting mechanism 106 of the invention can also be used on an electronic insulin pen having the motor drive module 101.

In operation, the drug delivery device 10 would be activated by pressing a dose dial knob 109. A user can rotate the dose dial knob 109 to select and set a dosage (as displayed through a LCD display 111). After setting the dosage, the user can press the dose dial knob 109 to generate a dispense button signal to the control board 103 indicative of the dose to be expelled. The motor drive module 101 is operated under the control of the control board 103. The motor drive module 101 can drive the screw spindle 108 to move forward by way of a gear train (not illustrated). When the screw spindle 108 is in a fully extended portion in which as much medicament as possible has been expelled from the cartridge 112, the user detaches the cartridge holder 110 from the drug delivery device 10. The resetting mechanism 106 will release the screw spindle 108, and then the user can push back (retract) the screw spindle 108 to an initial position.

The resetting mechanism and the drug delivery device of the present invention can achieve the purpose of resetting the screw spindle by using fewer components, thus facilitating the production and assembly and being portable. Furthermore, the present invention also provides a more intuitive way for the user to replace the empty cartridge and reset the screw spindle.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A resetting mechanism for resetting a screw spindle of a drug delivery device, comprising:
   a driving element, comprising:
      two opposite driving pillars connected to a sidewall and disposed in a chamber;
   a limiting element movably engaged with the driving element, and two opposite clamping elements movably disposed on two sides of the screw spindle, each of the clamping elements comprising:
      a sliding base, wherein the sliding base has a guide rail and a recess, and
      a clamping jaw, connected to the sliding base and disposed in the chamber, wherein
   the opposite driving pillars slide in the guide rails along with the movement of the driving element;

when the driving element moves toward the limiting element, the driving pillars drive the two clamping elements to move toward the screw spindle to make the two clamping jaws clamp the screw spindle;

when the driving element moves away from the limiting element, the driving pillars drive the two clamping elements to move away from the screw spindle to make the two clamping jaws release the screw spindle.

2. The resetting mechanism according to claim 1, comprising:
the driving element, further comprising:
a base having an opening for the screw spindle to insert through;
a sidewall surrounding the base to form a chamber, wherein the sidewall has two opposite first notches and two opposite second notches, and
two opposite positioning pillars connected to the sidewall and disposed on the two opposite first notches.

3. The resetting mechanism according to claim 2, comprising:
the limiting element, further comprising:
an annular case, configured to cooperate the chamber wherein the annular case allows the screw spindle to insert therethrough;
two opposite limiting arms, connected to the annular case and configured to cooperate with the two opposite first notches, wherein each of the two opposite limiting arms includes a passage along a length direction of the each of the two opposite limiting arms, and
two opposite positioning blocks, connected to the annular case, the two positioning blocks corresponding to the two opposite second notches.

4. The resetting mechanism according to claim 3, further comprising:
two spring elements, sleeved on the two opposite positioning pillars and received in the passages.

5. The resetting mechanism according to claim 3, wherein each of the two opposite limiting arms includes a hook portion.

6. The resetting mechanism according to claim 1, wherein each of the guide rails extends away from a side of the sliding base near the screw spindle to a side of the sliding base away the screw spindle.

7. The resetting mechanism according to claim 1, wherein each of the clamping jaws has a clamping surface wherein the clamping surface includes at least one groove cooperating with a thread of the screw spindle.

8. The resetting mechanism according to claim 1, wherein the moving direction of the driving element is perpendicular to moving direction of the two opposite clamping elements.

9. The resetting mechanism according to claim 4, wherein when each of the two spring elements abuts against the driving element, each of the two spring elements apply to the driving element a thrust to move along a direction away from the limiting element.

10. The resetting mechanism according to claim 1, wherein the drug delivery device comprises a cylindrical case, wherein the outer wall of the cylindrical case has at least one slot for being jointed with a hook portion.

11. A drug delivery device, comprising:
an outer case;
a drug expelling mechanism, disposed in the outer case and configured to set and dispense a dose amount of drug to be expelled, wherein the drug expelling mechanism at least comprises a cylindrical case;
a resetting mechanism according to claim 1, disposed in the outer case and connected to one end of the cylindrical case; and
a screw spindle, inserted in the drug expelling mechanism and the resetting mechanism.

12. The drug delivery device according to claim 11, comprising:
the driving element, further comprising:
a base, having an opening for the screw spindle to insert through;
a sidewall, surrounding the base to form a chamber wherein the sidewall has two opposite first notches and two opposite second notches, and
two opposite positioning pillars, connected to the sidewall and disposed on the two opposite first notches.

13. The drug delivery device according to claim 12, comprising:
the limiting element, further comprising:
an annular case, configured to cooperate the chamber wherein the screw spindle is inserted through the annular case;
two opposite limiting arms, connected to the annular case and configured to cooperate with the two opposite first notches, wherein each of the two opposite limiting arms includes a passage along a length direction of the each of the two opposite limiting arms, and
two opposite positioning blocks, connected to the annular case, the two positioning blocks corresponding to the two opposite second notches.

14. The drug delivery device according to claim 13, comprising:
two spring elements, sleeved on the two opposite positioning pillars and received in the passages.

15. The drug delivery device according to claim 13, wherein each of the two opposite limiting arms includes a hook portion.

16. The drug delivery device according to claim 11, wherein each of the guide rails extends away from a side of the sliding base near the screw spindle to a side of the sliding base away the screw spindle.

17. The drug delivery device according to claim 11, wherein each of the clamping jaws has a clamping surface wherein the clamping surface includes at least one groove cooperating with a thread of the screw spindle.

18. The drug delivery device according to claim 11, wherein the moving direction of the driving element is perpendicular to the moving direction of the two opposite clamping elements.

19. The drug delivery device according to claim 14, wherein when each of the two spring elements abuts against the driving element, each of the two spring elements apply to the driving element a thrust to move along a direction away from the limiting element.

20. The drug delivery device according to claim 11, wherein the drug delivery device comprises a cylindrical case, wherein the outer wall of the cylindrical case has at least one slot for being jointed with a hook portion.

21. The drug delivery device according to claim 11, further comprising a cartridge holder, removably connected to the outer case, wherein the cartridge holder serves to hold a cartridge, and the screw spindle is operably engaged with a piston of the cartridge.

22. The drug delivery device according to claim 21, wherein when the cartridge holder is connected to the outer case, the cartridge abuts against the base of the driving element to make two clamping jaws clamp the screw spindle.

23. The drug delivery device according to claim 22, wherein when the cartridge holder is not connected to the outer case, the two clamping jaws release the screw spindle to allow the screw spindle retract back to an initial position in the drug expelling mechanism.

24. The drug delivery device according to claim 11, wherein the drug delivery device is an electronic insulin pen including a motor drive module.

* * * * *